(12) United States Patent
Coull et al.

(10) Patent No.: US 6,197,513 B1
(45) Date of Patent: Mar. 6, 2001

(54) PNA AND DNA CONJUGATES AND METHODS FOR PREPARATION THEREOF

(75) Inventors: James Coull, Westford; Richard Fitzpatrick, Marblehead, both of MA (US)

(73) Assignee: PE Corporation, Foster City, CA (US)

( * ) Notice: Subject to any disclaimer, the term of this patent is extended or adjusted under 35 U.S.C. 154(b) by 0 days.

(21) Appl. No.: 09/247,996

(22) Filed: Feb. 10, 1999

Related U.S. Application Data

(60) Provisional application No. 60/074,388, filed on Feb. 11, 1998, now abandoned.

(51) Int. Cl.$^7$ .................... C12Q 1/68; C07H 19/00; C07H 21/00; C07H 21/02; C07H 21/04
(52) U.S. Cl. .................... 435/6; 435/91.1; 435/91.2; 536/22.1; 536/23.1; 536/24.3; 536/24.33; 536/25.3; 536/25.31; 536/25.32; 536/25.33; 536/25.34
(58) Field of Search .................... 435/6, 91.1, 91.2; 536/22.1, 23.1, 24.3, 24.33, 25.3, 25.31, 25.32, 25.33, 25.34

(56) References Cited

U.S. PATENT DOCUMENTS 5,705,333 * 1/1998 Shah et al. .................... 435/6

FOREIGN PATENT DOCUMENTS

| WO 96/11205 | 4/1986 | (WO) |
| WO 92/00989 | 1/1992 | (WO) |
| WO 93/04701 | 3/1993 | (WO) |
| WO 94/04550 | 3/1994 | (WO) |
| WO 94/13325 | 6/1994 | (WO) |
| WO 96/06105 | 2/1996 | (WO) |
| WO 96/40685 | 12/1996 | (WO) |
| WO 96/40709 | 12/1996 | (WO) |
| WO 98/24933 | 6/1998 | (WO) |
| WO 99/05302 | 2/1999 | (WO) |

OTHER PUBLICATIONS

J. Chen et al., Chemical Abstracts, vol. 122, No. 5 (Jan. 30, 1995).
Hermanson, "Bioconjugate Techniques," Academic Press, Inc. (1996) pp. 110–112, 120–125, 144–145, 152–154, 169–181, 390–400, 429–436.
Andrus, "Chemical Method for 5' Non–Isotopic Labelling of PCR Probes and Primers," *PCR 2: A Practical Approach*, Oxford University Press, (1995) pp. 39–54.
Gildea et al., "PNA Solubility Enhancers," *Tetrahedron Letters*, vol. 39 (1998), pp. 7255–7258.
Koch et al., "PNA–Peptide Chimerae," *Tetrahedron Letters*, vol. 36 (1995), pp. 6933–6936.
Simmons et al., "Synthesis and Membrane Permeability of PNA–Peptide Conjugates," *Bioorganic & Medicinal Chemistry Letters*, vol. 7 (1997), pp. 3001–3006.
Van der Laan et al., "A Convenient Automated Solid–Phase Synthesis of PNA–(5')–DNA–(3')–PNA Chimera," *Tetrahedron Letters*, vol. 38 (1997) pp. 2249–2252.

* cited by examiner

*Primary Examiner*—Jezia Riley
(74) *Attorney, Agent, or Firm*—Testa, Hurwitz & Thibeault, LLP

(57) ABSTRACT

Disclosed herein are methods for linking a protein or other biomolecule containing a carboxylic acid moiety to a PNA or DNA probe molecule. The methods disclosed herein involve activating the carboxylic acid moiety with an activating agent and reacting the activated carboxylic acid moiety with a PNA or DNA probe having an arylamine or aminooxyacetyl moiety. Conjugates produced by these methods are also disclosed.

25 Claims, 7 Drawing Sheets

A = CO$_2$H, acid chloride, acid fluoride, nitrophenyl ester, pentachlorophenyl ester, NHS ester, etc.

R = (CH$_2$)$_n$ , (CH$_2$CH$_2$O)$_n$
n = 1-10

Z = CH$_2$, CO, SO$_2$, O, S

Y = trifluoroacetyl, Fmoc, trityl, MMT, DMT or protecting group

A = CO₂H, acid chloride, acid fluoride, nitrophenyl ester, pentachlorophenyl ester, NHS ester, etc.

R = $(CH_2)_n$, $(CH_2CH_2O)_n$
   n = 1-10

Z = $CH_2$, CO, $SO_2$, O, S

Y = trifluoroacetyl, Fmoc, trityl, MMT, DMT or protecting group

X = amide, urea, $CH_2$, O, R

R = $(CH_2)_n$, $(CH_2CH_2O)_n$
   n = 1-10

Y = trifluoroacetyl, Fmoc, trityl, MMT, DMT
    or protecting group

PNA AND DNA CONJUGATES AND METHODS FOR PREPARATION THEREOF This application claims the benefit of U.S. Ser. No. 60/074,388, filed Feb. 11, 1998, now abandoned, the entire disclosure of which is incorporated by reference herein.

BACKGROUND

Bioconjugates such as oligonucleotide-enzyme conjugates are employed in a wide variety of molecular biology applications and diagnostic assays. Such conjugates have traditionally been prepared by a variety of methods, such as glutaraldehyde crosslinking, maleimide-thiol coupling, isothiocyanate-amine coupling, and Schiff base formation/reduction. Each of these procedures involves multiple steps that require the enzyme, oligonucleotide, or both, to be modified with the appropriate linking moiety and then purified before being combined and reacted with each other. Often the modification reaction results in an unstable reactive enzyme or oligomer intermediate that must be purified and used immediately. For these and other reasons the yield of conjugate is highly variable when these techniques are used. Furthermore, a large excess of oligonucleotide is usually required, reaction times are lengthy, and several purification steps are needed to obtain a purified conjugate. Finally, in most instances a portion of the enzymatic activity is lost due to the nature of the chemical reactions, lengthy reaction times, and numerous purification steps.

One method of making peptide-protein conjugates utilizes carbodiimide activation of carboxyl residues on the protein to facilitate coupling with primary alkyl amino groups of the peptide (see Hermanson, Bioconjugate Techniques, Academic Press, 1996). Coupling occurs at a pH range of 4.7–7.0. The author notes that nonspecific side reactions such as self-polymerization of the peptide and protein are common under the conditions necessary to produce appreciable amounts of the desired conjugate. Moreover, it is often necessary to drive the reaction by employing a large relative molar excess of either the peptide or protein to be coupled. The need to use a large excess of peptide is likely due to protonation of the primary amino groups under the pH conditions (<7) required to activate the carboxylic acid groups by the carbodiimide. Thus, under low pH conditions only a small fraction of the peptide molecules present possess amino groups which are unprotonated and reactive towards the carbodiimide-activated carboxyl moieties of the protein. Furthermore, peptides which possess more than one amino group may become crosslinked to each other and to the protein at multiple sites. Crosslinking often alters the structure of a peptide so that its ability to serve as an immunogen or ligand in a diagnostic assay is compromised.

Synthetic oligonucleotides which contain a primary amino group are useful for preparing hybridization probes and may be linked to enzymes by a variety of methods as described by Hermanson (ibid). However, no discussion is made of using carbodiimides to activate protein carboxyl groups for direct in situ reaction with amino derivatized oligonucleotides. It is believed that primary amino groups on synthetic oligonucleotides are protonated and unreactive under the low pH conditions necessary to activate protein carboxyl groups. Thus, efficient carbodiimide mediated conjugation of an amino derivatized oligonucleotide to a protein is not possible.

For these reasons direct conjugates are expensive and difficult to make with reproducible results. This has prevented them from becoming commonplace tools in molecular biology and diagnostic applications despite the promise they hold for improving assay sensitivity and simplifying nucleic acid detection schemes.

SUMMARY OF THE INVENTION

The present invention provides a simple, single-step experimental protocol to prepare conjugate compounds. The methods of the present invention utilize fewer and less expensive reagents than traditional methods to produce conjugates with no loss of activity of the components.

The present invention is directed to methods for linking a protein to a probe molecule in which a carboxylic acid moiety of the protein is activated using an activating agent and the protein is reacted with a probe having a nucleophilic moiety (i.e., an arylamine or aminooxyacetyl moiety), under conditions sufficient to promote reaction of the activated carboxylic acid moiety with the nucleophilic moiety. In another embodiment, the present invention relates to methods for linking a probe to a solid phase having a carboxylic acid moiety.

The methods of the present invention can be utilized to produce "chimeric" conjugates of different biomolecules, including, for example, PNA-enzyme conjugates, PNA-antibody conjugates, PNA-peptide conjugates, PNA-DNA conjugates, DNA-enzyme conjugates, DNA-antibody conjugates, and DNA-peptide conjugates. In addition, the present methods can be used to link PNA- and DNA-oligomers to a solid phase having a carboxylic acid moiety.

The present invention is also directed to chemical linkers that can be utilized to make the chimeric conjugates using the methods described herein. In the case of linkers for making PNA conjugates, these linkers are termed "P-linkers." Generally, these conjugate compounds have the formula:

wherein:
R is a protein or a solid phase having a carboxylic acid moiety;
S is a bond, alkyl chain or a chemical spacer having the formula: $-((CD_2)_mO)_n-$;
  wherein: D is H, F, Cl, Br, I, or lower alkyl, and m and n are individually 1–10.
T is a bond, a carbonyl, or a thiocarbonyl;
Ar is a substituted aryl group, including phenyl, napthyl and the like, and including substituents $R_1-R_7$.
L is a linker comprising carbonyl, sulfone, or phosphate moieties; and
Z is PNA, DNA, or peptide.

In short, the invention provides a heretofore unappreciated method for preparing bioconjugates, especially DNA- and PNA-conjugates. Moreover, in accordance with the present teachings, the invention can also be utilized to prepare labelled PNA and DNA oligomers and to link PNA and DNA to a solid phase. Finally, as will be appreciated by the skilled practitioner, the invention can be used in kits to prepare conjugates, to synthesize custom conjugates, to prepare non-radioactive hybridization probes, and in a variety of diagnostic and related applications.

These and other objects, along with advantages and features of the invention disclosed herein, will be made more apparent from the description, drawings and claims that follow.

DETAILED DESCRIPTION OF THE INVENTION

Figure 1:
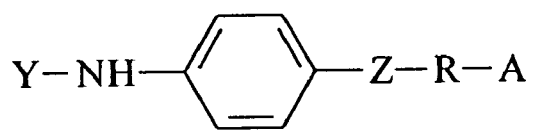
FIG. 1 shows the general structure for linker reagents with functional groups A to couple to PNA and peptides. Removal of protecting group Y from the resulting linker PNA or peptide then allows coupling of the arylamine group with a carboxyl group of a protein to form the conjugate.
Figure 2:
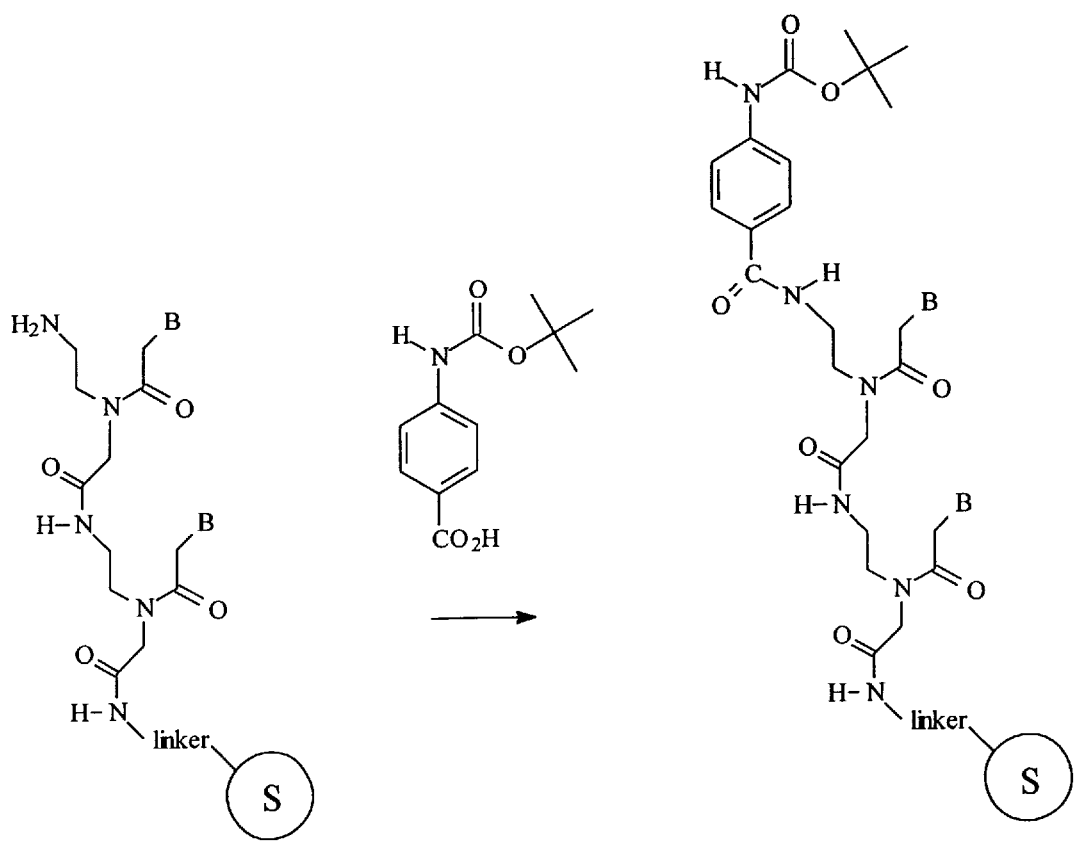
FIG. 2 shows a coupling reaction between linker reagent, N-tert-butoxycarbonyl-para-aminobenzoic acid, and the N-terminal amine of a PNA on a solid support. The coupling reagent may be EDC, HATU or other coupling reagents.
Figure 3:
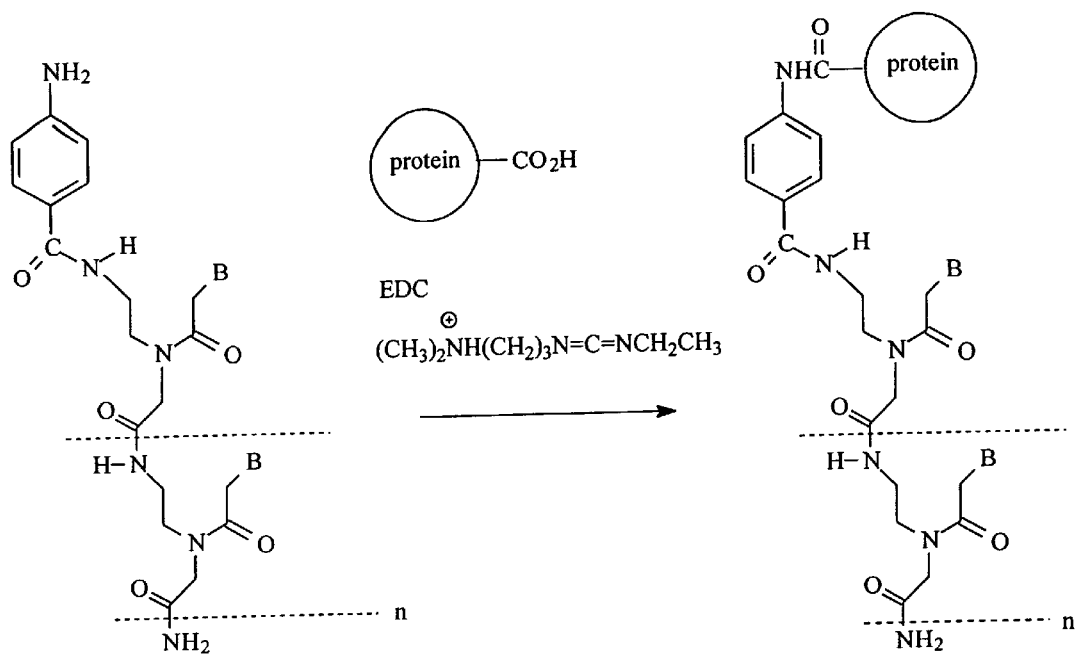
FIG. 3 shows a conjugation reaction between a PNA, a carboxy-containing protein, and an activating agent, EDC to form a protein-PNA conjugate.
Figure 4:
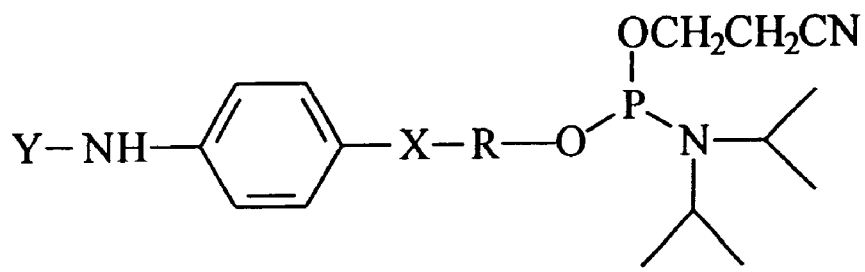
FIG. 4 shows the general structure of an arylamine phosphoramidite linker reagent for coupling to the 5' hydroxyl terminus of an oligonucleotide on a solid support. Removal of Y from the resulting linker-oligonucleotide then allows coupling of the arylamine group with a carboxyl group of a protein to form a protein-oligonucleotide conjugate.

In its broadest aspects, the present invention provides the skilled artisan with the analytical tools and technical know-how sufficient to produce bioconjugates. Guidance provided herein will facilitate methods for linking a protein to a probe molecule.

As used herein, the term "oligonucleotide" refers to polymers, such as DNA and RNA, of nucleotide monomers or nucleic acid analogs thereof, including double and single stranded deoxyribonucleotides, ribonucleotides, a-anomeric forms thereof, and the like. Usually the monomers are linked by phosphodiester linkages, where the term "phosphodiester linkage" refers to phosphodiester bonds or bonds including phosphate analogs thereof, including associated counterions, e.g., H+, NH4+, Na+. Oligonucleotides typically range in size from a few monomeric units, e.g. 5–40, to several thousands of monomeric units. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes deoxythymidine, unless otherwise noted.

"Nucleoside" refers to a compound consisting of a purine, deazapurine, or pyrimidine nucleobase, e.g., adenine, guanine, cytosine, uracil, thymine, deazaadenine, deazaguanosine, and the like, linked to a pentose at the 1'-position. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

"Nucleotide" refers to a phosphate ester of a nucleoside, e.g., a triphosphate ester, wherein the most common site of esterification is the hydroxyl group attached to the C-5 position of the pentose. A nucleotide is composed of three moieties: a sugar, a phosphate, and a nucleobase (Blackburn, G. and Gait, M. Eds. "DNA and RNA structure" in Nucleic Acids in Chemistry and Biology, 2nd Edition, (1996) Oxford University Press, pp. 15–81.). When part of a duplex, nucleotides are also referred to as "bases" or "base pairs".

The term "nucleic acid analogs" refers to analogs of nucleic acids made from monomeric nucleotide analog units, and possessing some of the qualities and properties associated with nucleic acids. Nucleic acid analogs may have modified (i) nucleobase moieties, e.g. C-5-propyne pyrimidine, pseudo-isocytidine and isoguanosine, (ii) sugar moieties, e.g. 2'-O-alkyl ribonucleotides, and/or (iii) internucleotide moieties, e.g. 3'-N-phosphoramidate (Englisch, U. and Gauss, D. "Chemically modified oligonucleotides as probes and inhibitors", Angew. Chem. Int. Ed. Engl. 30:613–29 (1991)).

A class of analogs where the sugar and internucleotide moieties have been replaced with an 2-aminoethylglycine amide backbone polymer is peptide nucleic acids PNA (Nielsen, P., Egholm, M., Berg, R. and Buchardt, O. "Sequence-selective recognition of DNA by strand displacement with a thymidine-substituted polyamide", Science 254:1497–1500 (1991)). PNA is represented by the structure:

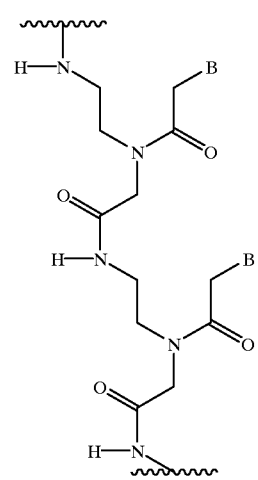

where B is a nucleobase or nucleobase analog.

The term "probe" refers to an oligonucleotide, a nucleic acid analog containing nucleobase analogs, sugar analogs, and/or internucleotide analogs, or a peptide. The probes employed in the present invention contain (or are modified to contain) a nucleophilic moiety. Generally, the nucleophilic moieties useful in the context of the present invention are those that have a pKa of less than about 7.0. Preferred nucleophilic moieties of this type are arylamine moieties and aminooxyacetyl moieties.

Specifically, the methods of the present invention are directed to linking a protein to a probe by:

(a) activating a carboxylic acid moiety on the protein with an activating agent to produce an activated carboxylic acid moiety on the protein; and (b) reacting the activated carboxylic acid moiety with the probe, wherein the probe contains a nucleophilic moiety selected from the group consisting of an arylamine and an aminooxyacetyl moiety, under conditions sufficient to promote reaction of the activated carboxylic acid moiety with the nucleophilic moiety.

The methods of the present invention can be generally employed to link probes to a variety of protein molecules, as will be appreciated by one skilled in the art. Preferred proteins for use in the invention are enzymes and antibodies. Preferred enzymes include alkaline phosphatase, galactosidase, horseradish peroxidase, and soybean peroxidase.

In the methods of the invention, a carboxylic acid moiety on the protein is activated by the addition of an activating agent. Activating agents include HATU (O-(7-azabenzotriazol-1-yl)-N,N,N',N'-tetramethyluronium hexafluorophosphate); HBTU (O-benzotriazol-1-yl)-N,N,N',N'-tetramethyluronium hexafluorophosphate); TBTU (2-(1H-benzotriazo-1-yl)-1-1,3,3-tetramethyluronium hexafluorophosphate); TFFH (N,N',N'',N''-tetramethyluronium 2-fluoro-hexafluorophosphate); BOP (benzotriazol-1-yloxytris(dimethylamino)phosphonium hexafluorophosphate); PyBOP (benzotriazole-1-yl-oxy-tris-pyrrolidino-phosphonium hexafluorophosphate; EEDQ (2-ethoxy-1-ethoxycarbonyl-1,2-dihydro-quinoline); DCC (dicyclohexylcarbodiimide); DIPCDI (diisopropylcarbodiimide); HOBt (1-hydroxybenzotriazole); N-hydroxysuccinimide; MSNT (1-(mesitylene-2-sulfonyl)-3-nitro-1H-1,2,4-triazole; aryl sulfonyl halides, e.g. triisopropylbenzenesulfonyl chloride. Preferred activating agents are carbodiimides. Most preferred activating agents are 1-ethyl-3-(3-dimethylaminopropyl) carbodiimide hydrochloride (EDC), and 1-cyclohexyl-3-(2-morpholinoethyl) carbodiimide (CDC).

The activated carboxylic acid moiety as described above reacts with the nucleophilic moiety on the probe, under conditions known to the skilled practitioner as sufficient to promote the reaction of the activated carboxylic acid moiety with the nucleophilic moiety. Under preferred reaction conditions, a relatively low pH is maintained, i.e., a pH less than about 6.5. Under traditional methods (i.e., at higher pH levels) it is believed that the activated carboxylic acid and/or the activating agent hydrolyze quickly, reducing the efficiency of the conjugation reaction.

Further, the skilled practitioner will appreciate that the use of a carbodiimide can often destroy enzyme activity. However, under the low pH conditions preferentially employed in the present invention, the destructive activity of carbodiimide can be substantially reduced or eliminated.

One skilled in the art will appreciate that the methods used to activate and conjugate the proteins should be selected to avoid destroying protein structure and activity. That is, in the case of enzyme conjugates, care should be taken so that the conjugation reaction does not destroy the enzyme active site or sterically hinder enzyme activity. "Exposed" carboxylic acid groups (i.e., those carboxylic acid moieties on the protein that are not associated with a region recognized as critical for protein activity) should be selected for activation.

While not wishing to be bound by theory, the Applicant(s) believe that combining a biomolecule having at least one nucleophile of pK less than 7, such as an arylamine group, with a carboxyl group containing protein such as an enzyme, in a buffered solution with a pH of 6.5, in the presence of an activating agent (i.e., carbodiimide), provides an efficient conjugation of the biomolecule to the protein because the nucleophile is substantially deprotonated and reactive under the low pH conditions most favorable for activation of the carboxyl group(s) of the protein. Applicant(s) have shown that in contrast to standard conjugation methods, only a small molar excess (as little as threefold) of biomolecule to protein is required to achieve high yield conjugation. As a result, Applicant(s) believe that a majority of the arylamine modified biomolecules in the reaction are reactive under the conditions of carboxyl activation. Moreover, Applicant(s) have shown that the conjugation chemistry proceeds rapidly and that the procedure is a "one pot," one step process which obviates the need to isolate or handle reactive biomolecule or protein intermediates.

The methods of the present invention can be used to prepare a variety of bioconjugates. The methods described herein are especially useful for preparing chimeric conjugates, i.e., conjugates of two dissimilar molecules not normally formed together. Bioconjugates contemplated by the present invention include: PNA-enzyme conjugates, PNA-antibody conjugates, PNA-peptide conjugates, PNA-DNA conjugates, DNA-enzyme conjugates, DNA-antibody conjugates, DNA-peptide conjugates and antibody-enzyme conjugates.

Following the conjugation reaction, the conjugate can be isolated by a variety of methods familiar to those skilled in the art. For example, the reaction mixture can be applied to a column chromatography system and separated by size-exclusion.

In addition, as one skilled in the art will appreciate, the methods of the present invention can be adapted to link a DNA or PNA molecule to a solid phase having a carboxylic acid moiety. Similarly, the methods described herein can be utilize to link other sensitive small molecules or haptens to a PNA or DNA probe.

The present invention is also directed to specific conjugate compounds that can be prepared by the methods discussed herein. Generally, these compounds have the formula:

wherein:

R is a protein or a solid phase having a carboxylic acid moiety;

S is a bond, alkyl chain or a chemical spacer having the formula: —$((CD_2)_mO)_n$—;

wherein: D is H, F, Cl, Br, I, or lower alkyl, and m and n are individually 1–10.

T is a bond, a carbonyl, or a thiocarbonyl;

Ar is a substituted aryl group, including phenyl, napthyl and the like, and including substituents $R_1$–$R_7$.

L is a linker comprising carbonyl, sulfone, or phosphate moieties; and

Z is PNA, DNA, or peptide.

These compounds can be represented by the formulas:

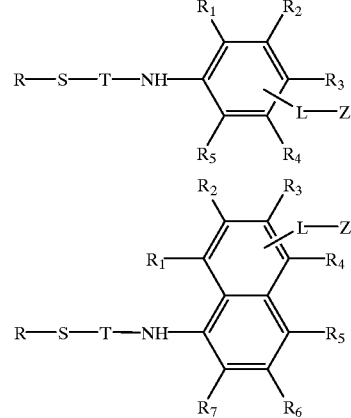

wherein $R_1$–$R_7$ are independently selected from the group of linker L, hydrogen, hydroxyl, fluorine, chlorine, bromine, iodine, lower alkyl, haloalkyl, alkoxy, haloalkoxy, alkylthio, haloalkylthio, alkylsulfoxy, alkylsulfo, nitro, cyano, alkoxycarbonyl, phenyl, substituted phenyl, phenoxy, substituted phenoxy, aryl, benzensulfonyl, benzyl, substituted benzyl, benzyloxy, substituted benzyloxy, heteroaryl, substituted heteroaryl, allyl, allyloxy, amino, amino carbonyl, alkylamino, arylamino, dialkyl amino, sulfonate, amido, alkylamido, and fused cyclic systems. Examples of preferred conjugate compounds include:

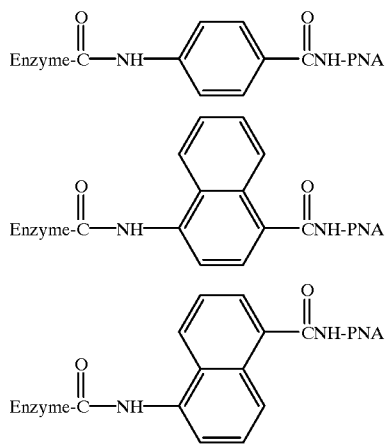

The present invention also relates to specialized linker compounds that may be used to modify probes (PNA or DNA) for use in the methods of making the conjugates of the present invention. An exemplary DNA linker reagent of the present invention is represented by the formula:

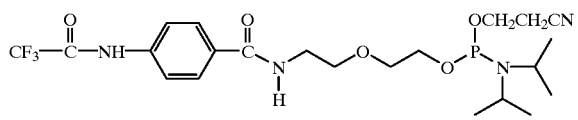

FIGS. 2, 3, 5 and 7 provide synthetic schemes useful to prepare the linker compounds contemplated by the present invention. Those skilled in the art will appreciate that the linker compounds of the present invention may be prepared by a variety of means and may then be employed in the methods of the invention to produce the desired conjugates.

The conjugates of the present invention can be utilized in a wide variety of biological assays and applications, including detection of target and hybridization assays such as Northern or Southern blotting. Detection of a target using oligonucleotide-enzyme conjugates occurs due to chemiluminescent decay, color or fluorescence formation as a result of to hydrolysis of a substrate molecule (e.g. a dioextane, acridine ester, dye molecule etc.) by the enzyme portion of the conjugate. For example, a Southern blot using restriction-enzyme digested DNA sample may be probed using an EDC-prepared alkaline phosphatase PNA conjugate (probe concentration at approximately 3 pmol/mL), under standard hybridization conditions (data not shown).

The present invention provides methods for the synthesis of PNA-enzyme conjugates by direct coupling of arylamine terminated PNA molecules to alkaline phosphatase in the presence of water soluble carbodiimide. The arylamine moiety at the terminus of the PNA is incorporated during solid-phase synthesis of the oligomer by employing a protected arylamine monomer. Thus, no extra steps are required post synthesis to introduce the arylamine group. The oligomer (5 equ.) is then combined with an enzyme, as obtained from the manufacturer (no buffer changes or modifications are necessary), and water soluble carbodiimide is added in an appropriate buffer (such as MES, pH 5.0) to promote reactions between the carboxyl groups on the enzyme and the aminophenyl group on the terminus of the PNA. The reaction is allowed to proceed for 30 minutes and then the mixture is applied to a short G-50 size exclusion column. The conjugate elutes within 5 minutes and consists of mainly the 1:1 PNA-alkaline phosphatase conjugate (as determined by UV spectroscopy).

Studies with different PNA molecules that have each been coupled a number of times have demonstrated excellent reproducibility. In addition, enzyme conjugates prepared by this method show no detectable loss of activity over the course of the conjugate reactions.

The conjugates may be employed in Southern and Northern blotting applications. The inventors have further found that improved results may be obtained in such applications by: (1) Lowering the temperature of the conjugation reactions to 0° C., (2) quenching unreacted carboxyls on the enzyme surface with glycine, and (3) using a one step hybridization solution to reduce background. The one step hybridization solution comprises a buffer, the conjugate, SDS, PEG and casein. The PEG serves to improve hybridization kinetics while the casein, an inexpensive phosphoprotein, serves to block reactive binding sites on the membrane. The use of the one step hybridization solution effectively shortens the time required (now only 1.5 hr) to use the conjugate since no "prehybridization" step is required to block the membrane before the conjugate is added.

Practice of the invention will be still more fully understood from the following examples which are presented herein for illustration only and should not be construed as limiting the invention in any way.

EXAMPLE 1

Synthesis of N-terminal arylamine-linked PNA

Automated synthesis of PNA was performed using an ABI Model 394 DNA/RNA synthesizer or 433A peptide synthesizer (Perkin-Elmer Co.) according to the general procedures described in the synthesizer manufacturer's Users Manual (also, Egholm, M., Buchardt, O., Christensen, L., Behrens, C., Freier, S., Driver, D., Berg, R. and Kim, S. "PNA hybridizes to complementary oligonucleotides obeying the Watson-Crick hydrogen bonding rules", Nature 365:566–68 (1993)).

PNA were synthesized at 2–5 μmole scale on an MBHA (methylbenzhydrylamine) linker, high-loaded polystyrene support, and with standard synthesis techniques and nucleobase ($A^{bz}$, $C^{bz}$, $G^{ibu}$, T) and primary amino (MMT, Fmoc or Boc) protecting groups, essentially as previously reported (Dueholm, K., Egholm, M., Behrens, C., Christensen, L., Hansen, H., Vulpius, T., Petersen, K., Berg, R., Nielsen, P. and Buchardt, O. "Synthesis of peptide nucleic acid monomers containing the four natural nucleobases: thymine, cytosine, adenine, and guanine and their oligomerization", J. Org. Chem. 59:5767–73 (1994).). A 3 ml reaction vessel is used at the 5 (mole scale with a total reaction volume of 440 (1.

PNA were prepared with a carboxy-terminal lysine on a MBHA-polystyrene solid support, by preloading with t-Boc-lys(Fmoc). PNA with carboxy-terminal amides were synthesized either directly on an MBHA support or on a MBHA support pre-loaded with the t-Boc T PNA monomer. All resins were loaded at approximately 0.1 to 0.25 mmole/g.

PNA oligomer $H_2N$-TCCTCCTT (1 (mole) on solid-support was synthesized by the above procedures. The PNA on polystyrene support was reacted with a mixture of (5 mg, 10 (mole) N-tert-butoxycarbonyl-para-aminobenzoic acid (FIG. 2), HATU (10 (mole), HOBt (10 (mole), 5 µl DIEA and 100 µl DMF and allowed to stand for 1 hour at room temperature. The support was then washed with DMF and CH$_2$Cl$_2$, cleaved with TFMSA (trifluoromethanesulfonic acid) at room temperature for 1 hour, and precipitated in ether to give N-p-aminobenzamide-PNA (H$_2$N-Ph-NH-TCCTCCTT), analyzed by reverse-phase HPLC and MALDI-TOF mass spectroscopy to confirm homogeneous purity and identity.

EXAMPLE 2

Synthesis of 5' arylamine-linked oligonucleotides

Generally, synthesis of oligonucleotides and nucleic acid analogs of the invention follow conventional teachings, preferably synthesized on an automated, solid-phase DNA synthesizer using phosphoramidite chemistry (Beaucage, 1992; Caruthers, 1983). The phosphoramidite method of oligonucleotide synthesis is a preferred method because of its efficient and rapid coupling and the stability of the starting nucleoside monomers. Synthesis is typically performed with a growing polynucleotide chain attached to a solid support so that excess reagents in the liquid phase can be easily removed by filtration, thereby eliminating the need for purification steps between cycles. DNA phosphoramidite nucleoside monomers may be obtained from Perkin-Elmer Co. (Foster City, Calif.) and 2'-OMe RNA monomers may be obtained from Glen Research (Sterling, Va.). The nucleobase protecting groups may be benzoyl ($A^{bz}$ and $C^{bz}$) and dimethylformamidine ($G^{dmf}$) for both the DNA and 2'-OMe RNA nucleosides.

Figure 5:
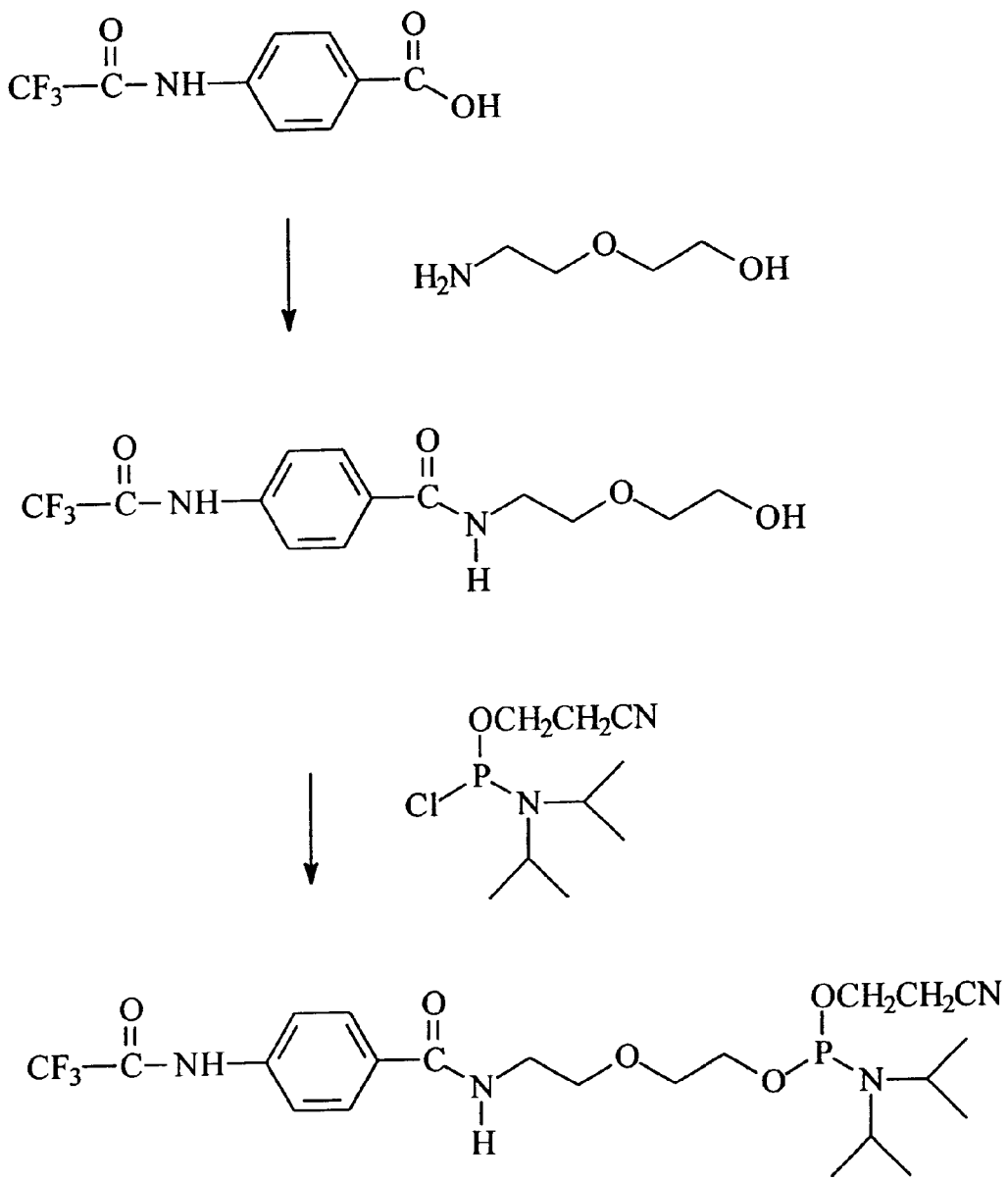
FIG. 5 shows a synthetic route to synthesis of a N-trifluoroacetyl, arylamine phosphoramidite linker reagent.
Figure 6:
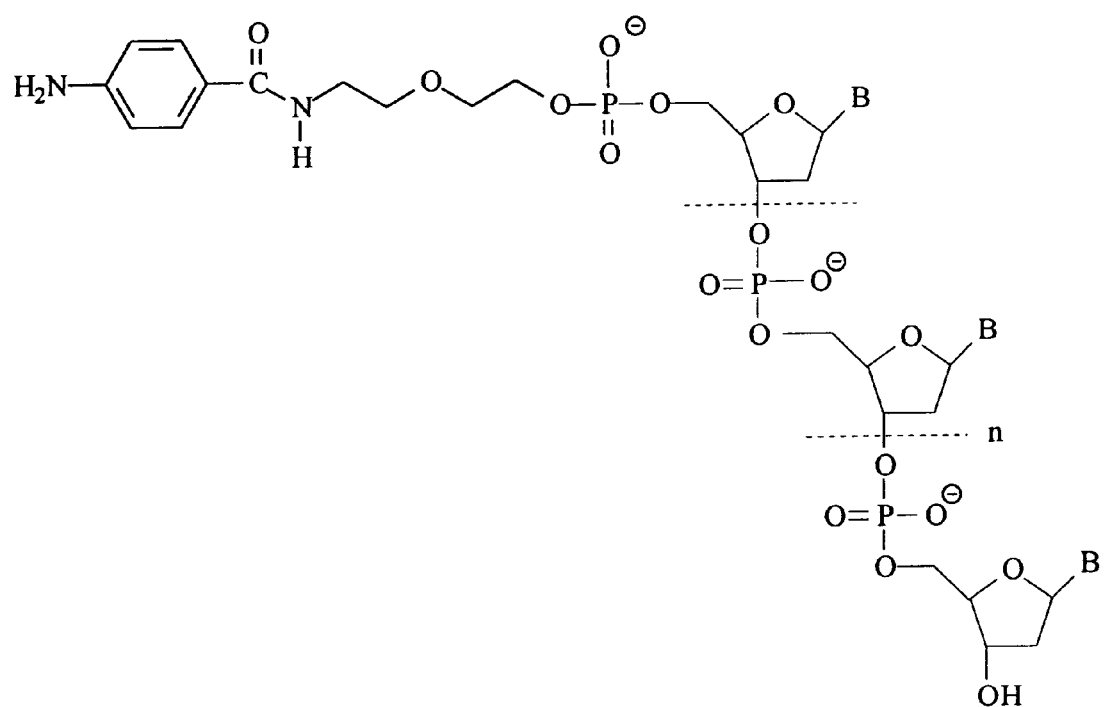
FIG. 6 shows a general structure of a linker-oligonucleotide that results from coupling of a N-protected, arylamine phosphoramidite to an oligonucleotide on a solid-support, followed by cleavage and deprotection.
Figure 7:
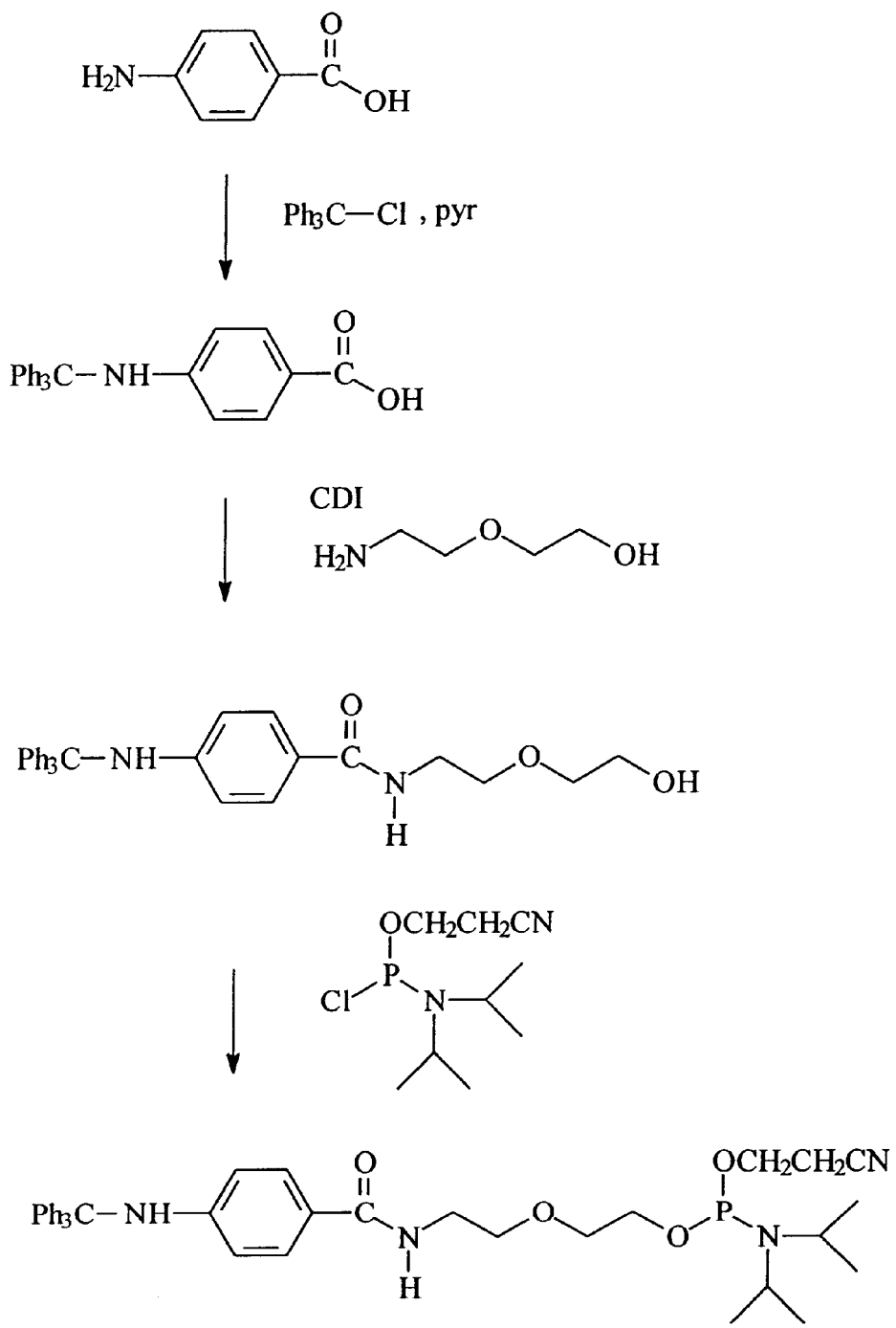
FIG. 7 shows a synthetic route to synthesis of a N-triphenylmethyl, arylamine phosphoramidite linker reagent.

For each coupling cycle of the synthesis at a 0.2 µmole scale, 40 µl of 0.1 M phosphoramidite nucleoside (ca. 3.5 mg) in acetonitrile is delivered concurrently with 120 µl of 0.5 M 5-H tetrazole in acetonitrile. Coupling times are 25 seconds for DNA phosphoramidites and 4 minutes for 2'-OMe RNA phosphoramidites and the arylamine phosphoramidite (FIG. 5). The arylamine phosphoramidite is added as the last monomer to complete the automated synthesis of a 5' arylamine oligonucleotide.

After completion of the synthesis, oligonucleotides may be cleaved from the support by treatment with concentrated ammonium hydroxide for 1 hr at room temperature as described in the Users Manual for the Applied Biosystems Model 394 DNA/RNA synthesizer. Base protecting groups may be removed by heating the mixture at 85° C. for 1 hr or at 65° C. for 3 h. The oligonucleotides can be analyzed and purified by reverse phase HPLC, anion-exchange HPLC, capillary gel electrophoresis, polyacrylamide gel electrophoresis, and other conventional techniques.

EXAMPLE 3

Preparation of peroxidase-PNA conjugate with N-terminal arylamine linked PNA 15-mer For the coupling procedure, 40 µg of soybean peroxidase, 1 nmol, (in 20 µL of 3M NaCl, 10 mM MgCl$_2$, 30 mM N-methylmorpholine, pH 2.6) was combined in a reaction tube with 12.5 µL DMF/water (3:7, v/v) and 2.3 nmol of an N-terminal arylamine linked PNA 15-mer (Example 1) dissolved in 7 µl of 1:1 DMF/water. The reaction tube was cooled on ice for 5 minutes and then 10 µL of 0.2 M aqueous morpholine-N-ethylsulfonic acid (MES) containing 1 mg of EDC was added. The reaction was allowed to proceed for 40 minutes at 0° C., then 7 µL of 0.5 M glycine, 0.25 M NaOH (in water) was added and the tube was incubated for an additional 20 minutes at 0° C.

Excess PNA was removed by transferring the contents of the reaction tube to the cup of a 30 k MWCO Ultrafree-MC centrifugal concentrator (Millipore). 50 µL of 1.5 M NaCl, 10 mM MgCl$_2$, 30 mM NMM in 1:1 DMF/water (v/v) was added and the cup was centrifuged at 5000×g for 5 minutes. To the filter cup was added 100 µL of 1.5 M NaCl, 10 mM MgCl$_2$, 30 mM NMM in 1:1 DMF/water (v/v) was added and the mixture was again centrifuged at 5000×g for 5 minutes. This addition and centrifugation was repeated and finally 50 µL of 1.5 M NaCl, 10 mM MgCl$_2$, 30 mM NMM in water was added to the cup. The mixture was then removed from the cup and diluted to 1 mL in water.

Conjugate concentration was estimated by reading absorbance at 260 nm. Conjugate concentration was estimated as 1266 pmol/mL as estimated by (AU2600.01)×10$^5$/probe length=pmol conjugate per µL.

EXAMPLE 4

Preparation of magnetic particles coupled with C-terminal arylamine linked PNA 15-mer Magnetic carboxyl modified (MGCM) particles from Seradyne (Cat. No. 2415-2105-050250; diameter—0.759 µM, COOH content—0.4696 meq./gm, parking area—2.7 Å/COOH, conc.—5% (gm/100 gm) solids) were pre-washed by removing 25 µl (1.25 mg MGCM particles) from a 5% stock and removing the azide buffer. The particles were washed 3 times with 50 µL 0.2M MES buffer at pH 5.25.

The coupling reaction was carried out by removing the buffer from the particles and adding 5 µL of 50% DMF solution. 15 µL (3 O.D.) of C-terminal arylamine linked PNA 15 mer in 50% DMF was added, along with 30 µL (1 mg) of EDC in 0.2 M MES (pH 5.25). The reaction tube was incubated for one hour at room temperature.

The reaction was quenched by removing buffer from the particles and adding 100 µL 5% (aqueous) 2-(2-aminoethoxy) ethanol (AEE) at pH 10. Alternatively, 100 µL 0.5 M glycinamide hydrochloride (pH 9.0) can be added. The reaction tube was then incubated for 30 minutes at room temperature.

The particles were washed by removing the buffer from the particles and washing 5 times with 600 µL 5% (aqueous) AEE at pH 10 with the last two washes being 30 minutes each, then washing 2 times with 600 µL dH$_2$O. Alternatively, the particles can be washed 5 times with 600 µL 0.5 M NaCl, 0.1 M Tris (pH 8.0), 20 mM EDTA, 0.5% Sarkosyl, 50% formamide, with the last two washes being 30 minutes each at 65° C., then washed 2 times with 600 µL dH$_2$O.

Particles can be stored in 1% aliquots in 0.1 M Tris (pH 7.4), 20 mM EDTA, 0.5% Sarkosyl, at 4° C.

EXAMPLE 5

Magnetic PNA particle capture assay

Particles coupled with a PNA 15-mer were prepared according to Example 4. Hybridization/capture/wash buffer (HCWB) was prepared having 100 mM NaCl, 50% formamide, 100 mM Tris pH 8, 20 mM EDTA and 0.5% Sarkosyl. Wash/antibody binding buffer (THT) was prepared having 50 mM Tris pH 7.2, 100 mM NaCl and 0.1% Tween 20.

200 µL positive or negative control targets (RNA transcripts—⅕ kb each) in HCWB was mixed with 100 µL particles coupled with PNA 15-mer in HCWB (12.5 µg particles/100 µL) and capture was allowed to proceed for 60 minutes at 47° C. Beads were separated for 5 minutes and aspirated. Beads were then washed 1 time by mixing with 500 µL HCWB, separated, then aspirated. Beads were washed 1 time by mixing with 500 µL THT, separated and aspirated.

300 µL Streptavidin/Horse radish peroxidase enzyme conjugate (Dako Code No. P0397) diluted 1:5000 in THT was added, mixed and incubated 30 minutes at room temperature (including time to transfer to new tubes). The mixture (particles and supernatant) was transferred to new tubes, the beads were separated for 4 minutes and aspirated. Beads were then washed twice by mixing with 500 μL THT, separated and aspirated.

100 μL TMB+ (Dako Code No. S1599) was added and the mixture was gently shaken and incubated for 15 minutes at 37° C. The mixture was separated and the supernatant was transferred to a microtiter plate. 100 μL 1 N $H_2SO_4$ was added. Absorbances were read in an ELISA reader at 450 nm with 650 nm as a reference. Assay results are presented in Table 1 below:

TABLE 1

| Target Level (No. of molecules) | 1E12 | 3E11 | 1E11 | 3E10 | No target added |
|---|---|---|---|---|---|
| Positive control target | 3.596 | 3.012 | 1.429 | 0.552 | 0.056 |
| Negative control target (1 mismatch) | 0.674 | 0.210 | 0.047 | 0.074 | 0.050 |

EXAMPLE 6

Synthesis of Magnetic Oligo(dT)20 using P-Linker Oligo (dT)20

110 mg carboxyl-terminated BioMag (6.1 mL of 20 mg/mL solution) was transferred to a polypropylene container and the paramagnetic particles were separated using a magnetic source, with the liquid being decanted off. Particles were washed 3 times with 6.1 mL of 0.1 M MES buffer at pH 5.5. The washed particles were then reconstituted to the original volume (6.1 mL) with MES buffer.

176 mg EDC was then added to the particles and the mixture was vortexed to dissolve the EDC and mixed on a rotator for 30 minutes at room temperature.

The particles were magnetically separated and the liquid was decanted. Particles were washed 3 times with 6.1 mL MES buffer, then reconstituted to the original volume of 6.1 mL with MES buffer.

5 mg of 5' arylamine-$T_{20}$ oligonucleotide (Example 2) in 0.8 ml DI water was added to the particle mixture and vortexed to mix. Particles were immediately separated with a magnet and 100 (L of liquid was removed for coupling efficiency determination. The mixture was vortexed to resuspend the particles, and placed on a rotator to continue mixing overnight at room temperature.

The particles were then magnetically separated and the liquid was removed (and retained for coupling efficiency determination). The particles were washed two times with 6.1 mL DI water. 6.1 mL 0.1 M $NaH_2PO_4$ was added to the particles and then mixed on a rotator for 30 minutes at room temperature.

The particles were magnetically separated and the liquid was decanted off. The particles were then washed 6 times with 20 mL MES buffer and reconstituted to 5 mg/mL with 0.1 M Tris buffer, pH 7.0.

The estimated coupling efficiency was 47% as determined by change in absorbance at 260 nm of the reaction solution: OD260 initial (1:100)=0.093; OD260 final (1:100)=0.049.

% coupling efficiency=(0.093–0.049)/(0.093)×100

Those of ordinary skill in the art will be able to ascertain, using no more than routine experimentation, many equivalents of the specific embodiments of the invention described herein. These and all other equivalents are intended to be encompassed by the following claims:

What is claimed is:

1. A method of linking a protein to a probe, said method comprising the steps of:
   (a) activating a carboxylic acid moiety on said protein with a carbodiimide to produce an activated carboxylic acid moiety on said protein; and
   (b) reacting said activated carboxylic acid moiety with less than or equal to 5 molar equivalents of said probe comprising an arylamine, under conditions sufficient to promote reaction of said activated carboxylic acid moiety with said arylamine to link said protein to said probe.

2. The method of claim 1 wherein said probe is PNA.
3. The method of claim 1 wherein said probe is DNA.
4. The method of claim 1 wherein said probe is a peptide.
5. The method of claim 1 wherein said protein is an enzyme.
6. The method of claim 5 wherein said enzyme is selected from the group consisting of alkaline phosphatase, galactosidase, horseradish peroxidase, and soybean peroxidase.
7. The method of claim 1 wherein said protein is an antibody.
8. The method of claim 1 wherein said carbodiimide is 1-ethyl-3-(3-dimethylaminopropyl) carbodiimide hydrochloride.
9. The method claim 1 wherein said carbodiimide is 1-cyclohexyl-3-(2-morpholinoethyl) carbodiimide.
10. The method of claim 1 wherein steps (a) and (b) are carried out at a pH of less than or equal to 6.5.
11. A method of linking a probe to a solid phase having a carboxylic acid moiety, said method comprising the steps of:
    (a) activating said carboxylic acid moiety with a carbodiimide to produce an activated carboxylic acid moiety; and
    (b) reacting said activated carboxylic acid moiety with less than or equal to 5 molar equivalents of said probe comprising an arylamine moiety, under conditions sufficient to promote reaction of said activated carboxylic acid moiety with said arylamine to link said probe to said solid phase.
12. The method of claim 11 wherein said probe is PNA.
13. The method of claim 11 wherein said probe is DNA.
14. The method of claim 11 wherein said probe is a peptide.
15. The method of claim 11 wherein said carbodiimide is 1-ethyl-3-(3-dimethylaminopropyl) carbodiimide hydrochloride.
16. The method claim 11 wherein said carbodiimide is 1-cyclohexyl-3-(2-morpholinoethyl) carbodiimide.
17. The method of claim 11 wherein steps (a) and (b) are carried out at a pH of less than or equal to 6.5.
18. A linker reagent having the formula:

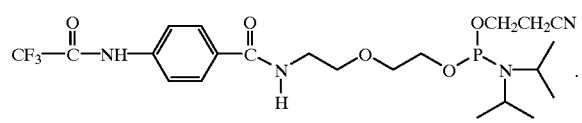

19. The method of claim 1 wherein step (b) comprises reacting said activated carboxylic acid moiety with less than or equal to 3 molar equivalents of said probe.
20. The method of claim 11 wherein step (b) comprises reacting said activated carboxylic acid moiety with less than or equal to 3 molar equivalents of said probe.

21. A method of linking a protein to a probe comprising the steps of:
   (a) activating a carboxylic acid moiety on a protein with a carbodiimide to produce an activated carboxylic acid moiety; and
   (b) reacting the activated carboxylic acid moiety with a probe comprising an arylamine, under conditions sufficient to promote reaction of the activated carboxylic acid moiety with the arylamine to link the protein to the probe,
   wherein steps (a) and (b) are carried out at a pH of less than or equal to 4.

22. A method of linking a probe to a solid phase comprising the steps of:
   (a) providing a solid phase having a carboxylic acid moiety;
   (b) activating the carboxylic acid moiety with a carbodiimide to produce an activated carboxylic acid moiety; and
   (c) reacting the activated carboxylic acid moiety with a probe comprising an arylamine, under conditions sufficient to promote reaction of the activated carboxylic acid moiety with the arylamine to link the probe to the solid phase,
   wherein steps (b) and (c) are conducted at a pH of less than or equal to 4.

23. A compound having the formula:

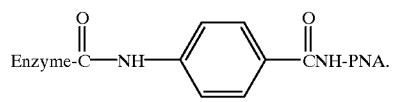

24. A compound having the formula:

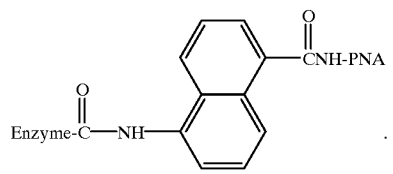

25. A compound having the formula:

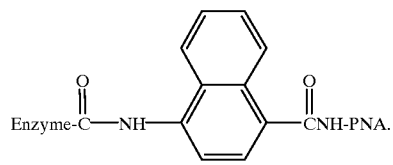

* * * * *